United States Patent
Seco et al.

(10) Patent No.: US 12,285,633 B2
(45) Date of Patent: Apr. 29, 2025

(54) DEVICE AND A METHOD FOR MONITORING A TREATMENT OF A BODY PART OF A PATIENT WITH PARTICLES

(71) Applicant: Deutsches Krebsforschungszentrum, Heidelberg (DE)

(72) Inventors: Joao Seco, Heidelberg (DE); Paulo Jorge Magalhaes Martins, Heidelberg (DE); Riccardo Dal Bello, Heidelberg (DE)

(73) Assignee: Deutsches Krebsforschungszentrum, Heidelberg (DE)

( * ) Notice: Subject to any disclaimer, the term of this patent is extended or adjusted under 35 U.S.C. 154(b) by 0 days.

(21) Appl. No.: 17/597,624

(22) PCT Filed: Jul. 16, 2020

(86) PCT No.: PCT/EP2020/070128
§ 371 (c)(1),
(2) Date: Jan. 14, 2022

(87) PCT Pub. No.: WO2021/009281
PCT Pub. Date: Jan. 21, 2021

(65) Prior Publication Data
US 2022/0249872 A1 Aug. 11, 2022

(30) Foreign Application Priority Data
Jul. 17, 2019 (EP) .................................... 19186728

(51) Int. Cl.
*A61N 5/10* (2006.01)
(52) U.S. Cl.
CPC ......... *A61N 5/1069* (2013.01); *A61N 5/1065* (2013.01); *A61N 5/1071* (2013.01);
(Continued)

(58) Field of Classification Search
CPC .. A61N 5/1069; A61N 5/1065; A61N 5/1071; A61N 5/1081; A61N 2005/1074;
(Continued)

(56) References Cited

U.S. PATENT DOCUMENTS

2006/0113482 A1 6/2006 Pelizzari et al.
2011/0057110 A1 3/2011 Testa et al.
(Continued)

FOREIGN PATENT DOCUMENTS

EP 2078537 A1 7/2009
EP 2950119 A1 12/2015
(Continued)

OTHER PUBLICATIONS

Min et al., Development of array-type prompt gamma measurement system for in vivo range verification in proton therapy, Med. Phys. 39(4), 8 pages, Apr. 1, 2012.
(Continued)

*Primary Examiner* — Marcus H Taningco
(74) *Attorney, Agent, or Firm* — Woodard, Emhardt, Henry, Reeves & Wagner, LLP

(57) ABSTRACT

A device (110) and a method for monitoring a treatment of a body part (112) of a patient (114) with a beam (116) comprising particles (118) are disclosed. Herein, the device (110) comprises—a beam delivering unit (120) designated for delivering a beam (116) comprising particles (118) and adjusting a direction (124) of propagation of the beam (116) onto a body part (112) of a patient (114); and—a verification unit (130) designated for verifying a range and a dose delivery of the particles (118) provided by the beam (116) to the body part (112) of the patient (114) by determining information about prompt-gamma radiation (140) generated by an interaction of the particles (118) with the body part (112) of the patient (114) at at least two individual interac-
(Continued)

tion points (150), wherein the verification unit (130) comprises a symmetry axis (149) which is symmetrical with respect to the at least two individual interaction points (150) and which is located perpendicular with respect to the direction (124) of the propagation of the beam (116). The device (110) and the method may be used in the field of particle therapy, specifically for verifying a range and a dose delivery of the particles (118) provided by the beam (116) to the body part (112) of a patient (114), especially towards a tumorous tissue of the patient (114).

14 Claims, 4 Drawing Sheets

(52) U.S. Cl.
CPC .... *A61N 5/1081* (2013.01); *A61N 2005/1074* (2013.01); *A61N 2005/1087* (2013.01); *A61N 2005/109* (2013.01)

(58) Field of Classification Search
CPC ...... A61N 2005/1087; A61N 2005/109; A61N 5/1048; A61N 5/1077; A61N 2005/1019
See application file for complete search history.

(56) References Cited

U.S. PATENT DOCUMENTS

| | | | |
|---|---|---|---|
| 2011/0186720 A1* | 8/2011 | Jongen | G01T 1/1642 250/361 R |
| 2011/0284757 A1* | 11/2011 | Butuceanu | G01T 1/185 250/389 |
| 2014/0145088 A1* | 5/2014 | Prieels | A61N 5/1048 250/393 |
| 2015/0087882 A1* | 3/2015 | Pausch | A61N 5/1067 600/1 |
| 2015/0297917 A1 | 10/2015 | Beekman et al. | |
| 2015/0321025 A1 | 11/2015 | Freud et al. | |
| 2017/0203125 A1* | 7/2017 | Amato | A61N 5/1039 |
| 2020/0316408 A1* | 10/2020 | Jacques | A61N 5/1079 |

FOREIGN PATENT DOCUMENTS

| | | |
|---|---|---|
| EP | 2977083 A1 | 1/2016 |
| JP | 2009172261 A | 8/2009 |
| JP | 2015502188 A | 1/2015 |
| JP | 2010032451 A | 2/2020 |
| WO | 2012011083 A1 | 1/2012 |
| WO | 2012104416 A1 | 8/2012 |
| WO | 2012152938 A2 | 11/2012 |
| WO | 2015040225 A1 | 3/2015 |
| WO | 2017156113 A1 | 9/2017 |
| WO | 2019224215 A1 | 11/2019 |

OTHER PUBLICATIONS

Rusiecka et al., Determination of Gamma Angular Distribution from the Shape of Spectral Line for the First Excited State of Carbon Nucleus, World Journal of Nuclear Science and Technology, vol. 6, pp. 63-70, 8 pages, Jan. 11, 2016.

Richter et al., First clinical application of a prompt gamma based in vivo proton range verification system, Radiotherapy and Oncology 118, p. 232-237, 6 pages, Jan. 13, 2016.

Xie et al., Prompt Gamma Imaging for In Vivo Range Verification of Pencil Beam Scanning Proton Therapy, Radiation Oncology, vol. 99, p. 210-218, 9 pages, May 3, 2017.

Krimmer et al., Prompt-gamma monitoring in hadrontherapy: A review, Nuclear Instruments and Methods in Physics Research Section A: Accelerators, Spectrometers, Detectors and Associated Equipment 878, pp. 58-73, 16 pages, Jan. 1, 2018.

Rusiecka et al., Shape of the spectral line and gamma angular distribution of the 12C(p, p' gamma4,44)12c reaction, Acta Physica Polonica B, vol. 49 (9), 1637, 17 pages, Jul. 17, 2018.

Hueso-Gonzalez et al., A full-scale clinical prototype for proton range verification using prompt gamma-ray spectroscopy, Phys. Med. Biol. 63, 185019, 39 pages, Sep. 17, 2018.

Kiener, Shape and angular distribution of the 4.439-MeV gamma-ray line from proton inelastic scattering off12C, Physical Review C 99, 014605, 33 pages, Jan. 7, 2019.

* cited by examiner

DEVICE AND A METHOD FOR MONITORING A TREATMENT OF A BODY PART OF A PATIENT WITH PARTICLES

TECHNICAL FIELD OF THE INVENTION

The present invention relates to a device and a method for monitoring a treatment of a body part of a patient with a beam comprising particles. The device and the method according to the present invention may, preferably, be used in the field of ion beam therapy, specifically for verifying a range and a dose delivery of the particles provided by the beam to the body part of a patient, especially towards a tumorous tissue of the patient. However, other kinds of applications are also possible.

RELATED ART

Particle therapy with hadron beams, wherein the hadrons are ions, specifically selected from protons or from ions of helium, carbon or oxygen, or neutrons, has a high clinical potential in terms of efficacy and effectiveness. Herein, carbon ion beams are, particularly, promising since they exhibit reduced lateral spread and increased biological effect. Herein, a synchrotron is, typically, used as main accelerator for the particle to energies above 50 MeV, wherein, for clinical use, maximum energies are, usually, between 230 and 250 MeV/u but may also assume a value up to 515 MeV/u. The accelerated particle beam is, subsequently, transported towards at least one patient treatment room by employing a series of vacuum tubes as well as shaping and focusing magnets. In the treatment room, the beam may either be a fixed beam having a fixed direction with respect to a horizontal or a vertical orientation or to a specific angle, or can be delivered to any desirable direction by applying a rotational gantry. Herein, the gantry refers to a unit which is adapted to fully rotate over 360° for delivering the beam at the angle specified by the treatment. Further, the beam may be provided by a delivery nozzle which is designed for shaping the beam in a fashion that it conforms to a stereometry of the tumor, preferably, to both a cross-sectional shape of the tumor and a shape of the distal surface, for which purpose range modulators, degraders, collimators, and compensators may be used. Active magnetic scanning may also be possible. In general, the patient may be properly positioned to receive the treatment. For this purpose, robotic instrumentation designated to position the patient accurately with regard to six directions of movement or rotation may be used. Preferably, a therapy control system may, further, be used as interface for controlling and monitoring the treatment.

In general, it is desirable to prevent healthy organs of a patient to receive radiation, in particular the particles provided by the beam. For this purpose, it is known to employ a so-called "Bragg peak" to significantly reduce side effects to the patient. As generally used, the term "Bragg peak" refers to a pronounced peak within a so-called "Bragg curve" which denotes a graphical representation of the energy loss of the incident beam with respect to a traveling distance of the beam through matter, specifically through the tissue of the patient. Hadron beams exhibit the advantageous effect that the Bragg peak occurs immediately before the hadrons come to rest within the matter, in particular within the tissue of the patient. Thus, in order to solve the above-indicated problem of preventing healthy organs from receiving radiation, an improved range control with respect to a location of the Bragg peak within the tissue is desirable. Herein, it is, particularly, intended to apply a kind of range verification which is capable of reducing range uncertainties and, therefore, safety margins as far as possible.

Among the techniques which are used for a range verification of ion hadron beams in the tissue of a patient, prompt-gamma imaging has been demonstrated in the clinical environment as the one with the most promising features for a real-time tracking of the ion beam. Conversely to other range verification techniques, such as positron emission tomography that relies on an emission of photons on a much longer time scale, prompt-gamma imaging allows, due to a nearly instantaneous emission of the gamma radiation resulting from a nuclear interaction of the hadron beam with the tissue, a prompt detection of emitted gamma radiation. However, it has been described that the prompt-gamma radiation is not isotropic but rather involves a higher yield with respect to backward-peaked and forward-peaked gamma radiation. Further, the desired range verification turned out to be more complex due to a presence of fragments which occur after the Bragg peak in beam direction.

J. Krimmer, D. Dauvergne, J. M. Létang, and É. Testa, *Prompt-gamma monitoring in hadrontherapy: A review*, Nuclear Instruments and Methods in Physics Research Section A: Accelerators, Spectrometers, Detectors and Associated Equipment 878, 2018, pp. 58-73, present a review and discuss the state of the art for all techniques using a detection of prompt-gamma radiation to improve the quality assurance in hadron therapy. Herein, secondary radiation emission induced by nuclear reactions is correlated to the path of ions in matter. Therefore, such penetrating radiation can be used for in vivo control of hadron therapy treatments, for which a primary beam is absorbed inside a patient. Among secondary radiation emission, prompt-gamma radiation was proposed for real-time verification of ion range. Such verification is a desired condition to reduce uncertainties in treatment planning. This review covers efforts which have been undertaken worldwide for more than a decade in order to promote prompt-gamma radiation based devices to be used in clinical conditions. Dedicated cameras are necessary to overcome the challenges of a broad- and high-energy distribution, a large background, high instantaneous count rates, and compatibility constraints with patient irradiation. Several types of prompt-gamma imaging devices have been proposed which are either physically-collimated or electronically collimated. In addition, other methods than direct prompt-gamma imaging were proposed, which are based on specific counting using either time-of-flight or photon energy measurements.

Fernando Hueso-González, Moritz Rabe, Thomas A Ruggieri, Thomas Bortfeld and Joost M Verburg, *A full-scale clinical prototype for proton range verification using prompt gamma-ray spectroscopy*, Phys. Med. Biol. 63, 2018, 185019, present a full-scale clinical prototype system for in vivo range verification of proton pencil-beams using the prompt gamma-ray spectroscopy method. The detection system consists of eight $LaBr_3$ scintillators and a tungsten collimator, mounted on a rotating frame. Custom electronics and calibration algorithms have been developed for measurement of energy- and time-resolved gamma-ray spectra during proton irradiation at a clinical dose rate. Using experimentally determined nuclear reaction cross-sections and a GPU-accelerated Monte Carlo simulation, a detailed model of the expected gamma-ray emissions is created for each individual pencil-beam. The absolute range of the proton pencil-beams is determined by minimizing the discrepancy between the measurement and this model, leaving the absolute range of the beam and the elemental concentrations of the irradiated matter as free parameters. The system was characterized in a clinical-like situation by irradiating different phantoms with a scanning pencil-beam. A dose of 0.9 Gy was delivered to a 5×10×10 $cm^3$ target with a beam current of 2 nA incident on a phantom. Different range shifters and materials were used to test the robustness of the verification method and to calculate the accuracy of the detected range. The absolute proton range was determined for each spot of the distal energy layer with a mean statistical precision of 1.1 mm at a 95% confidence level and a mean systematic deviation of 0.5 mm, when aggregating pencil-beam spots within a cylindrical region of 10 mm radius and 10 mm depth. Small range errors deliberately introduced were successfully detected and even large differences in the elemental composition do not affect the range verification accuracy. As a result, this system is suitable for range verification during patient treatments in clinical studies. However, this system is designed for proton beams accelerated at cyclotrons in which a well-correlated arrival time of the incident protons with the radio frequency of the cyclotron can be observed.

Yunhe Xie, El Hassane Bentefour, Guillaume Janssens, Julien Smeets, Francois Vander Stappen, Lucian Hotoiu, Lingshu Yin, Derek Dolney, Stephen Avery, Fionnbarr O'Grady, Damien Prieels, James McDonough, Timothy D. Solberg, Robert A. Lustig, Alexander Lin, and Boon-Keng K. Teo, *Prompt Gamma Imaging for In Vivo Range Verification of Pencil Beam Scanning Proton Therapy*, Radiation Oncology, Vol. 99 (2017), p. 210-218, report clinical results and value assessment of prompt-gamma imaging for in vivo proton range verification in a pencil-beam scanning mode which is, specifically, designed for a use in cyclotrons. A stand-alone, trolley-mounted, prototype prompt-gamma camera utilizing a knife-edge slit collimator design was used for recording the prompt-gamma signal as emitted along proton tracks during delivery of proton therapy for a brain cancer patient. The recorded prompt-gamma depth detection profiles of individual pencil-beam spots were compared with expected profiles simulated from a treatment plan.

Chul Hee Min, Han Rim Lee, Chan Hyeong Kim, and Se Byeong Lee, *Development of array-type prompt gamma measurement system for in vivo range verification in proton therapy*, Med. Phys. 39(4), 2012, to effectively measure prompt gammas against the background gammas, employed Monte Carlo simulations with an MCNPX code in optimizing the configuration of the measurement system, and also used a Monte Carlo method to understand the effect of the background gammas, mainly neutron capture gammas, in the measured gamma distribution. To reduce the effect of the background gammas, the optimized energy window of 4-10 MeV in measuring the prompt gammas was employed. A parameterized source was used to maximize computation speed in the optimization study. A simplified test measurement system, incorporating a single CsI(Tl) scintillation detector, a multi-slit collimation system, and a motion system designated for moving only one detector from one measurement location to the next, was constructed and applied to therapeutic proton beams of 80-220 MeV. For accurate determination of the distal dose edge, the sigmoidal curve-fitting method was applied to the measured distributions of the prompt gammas, and then, the location of the half-value between the maximum and minimum value in the curve-fitting was determined as the distal dose edge and compared with the beam range assessed by the proton dose distribution.

Christian Richter, Guntram Pausch, Steffen Barczyk, Marlen Priegnitz, Isabell Keitz, Julia Thiele, Julien Smeets, Francois Vander Stappen, Luca Bombelli, Carlo Fiorini, Lucian Hotoiu, Irene Perali, Damien Prieels, Wolfgang Enghardt, and Michael Baumann, *First clinical application of a prompt gamma based in vivo proton range verification system*, Radiotherapy and Oncology 118, p. 232-237, 2016, describe using a prototype of a knife-edge shaped slit camera to measure the prompt gamma ray depth distribution during a proton treatment of a head and neck tumor for seven consecutive fractions. Inter-fractional variations of the prompt gamma profile were evaluated. For three fractions, in-room control CTs were acquired and evaluated for dose relevant changes.

K. Rusiecka, A. Wrońska, P. Bednarczyk, D. Böckenhoff, A. Bubak, S. Feyen, L. Kelleter, A. Konefał, K. Laihem, J. Leidner, A. Magiera, G. Obrzud, A. Stahl, M. Zięblińsk, *Determination of Gamma Angular Distribution from the Shape of Spectral Line for the First Excited State of Carbon Nucleus*, World Journal of Nuclear Science and Technology, 2016, Vol. 6, pp. 63-70, and K. Rusiecka, A. Wrońska, A. Magiera, G. Gazdowicz, G. Obrzud, L. Kelleter, K. Laihem, J. Leidner, A. Stahl, A. Chrobak, A. Konefał, *Shape of the spectral line and gamma angular distribution of the 12C(p, p'$\gamma_{4.44}$)12c reaction*, Acta Physica Polonica B, Vol. 49 (9), 1637, 2018 present a model which explains a shape of a spectral line specific to a nuclear reaction used in prompt-gamma spectroscopy of proton beams with initial beam energies of 70.54 MeV and 88.97 MeV. The angular distribution of this gamma emission has two local maxima around 50 and 130 degrees. Furthermore, J. Kiener, *Shape and angular distribution of the 4.439-MeV γ-ray line from proton inelastic scattering off $^{12}C$*, Physical Review C 99, 014605, 2019, confirms these results with simulations from a 68-MeV proton beam stopped in human tissue.

EP 2 977 083 A1 discloses an apparatus and a method for charged hadron therapy verification by detecting and/or quantifying prompt gammas produced when irradiating a target with a charged hadron beam. The apparatus comprises a collimator provided with a slit-shaped portion configured to be arranged perpendicularly to the beam line and facing the target, a detection means suitable for detecting said prompt gammas and a calculation and representation means. In the apparatus and method of the invention, the slit is configured to allow the passage of prompt gammas emitted from a range of depths in said target, said depths being measured in the direction of the charged hadron beam. Furthermore, said detection means is configured to detect prompt gammas emitted from each location within said range, and said calculation and representation means is configured to derive from a detected prompt gamma a value representative of the dose at the location from where said prompt gamma is emitted, and to represent a dose-related distribution for a plurality of locations within said range.

US 2011/0057110 A1 discloses a method for real-time measurement of a local dose received by a region of a target upon bombardment of the target by an incident beam of hadrons which generates at least prompt-gamma rays and neutrons. The particles emitted by the target are measured by collimating the region of the target and by placing a detector at a distance from the region of the target to be measured. The detector is linked to a device for particle energy and time-of-flight measurement, such as to a hodoscope which comprises scintillating fibers or a polycrystalline diamond detector. The number of prompt-gamma rays received by the detector is determined by selecting the recorded events, and a two-directional charged-particle detection system, placed in the beam of incident hadrons before the target, is used so as to obtain the transverse position of the incident hadrons in order to provide spatial information of the beam.

US 2015/0321025 A1 discloses an apparatus and method for charged hadron therapy verification. The apparatus comprises a collimator comprising a plurality of collimator slabs of a given thickness, spaced apart so as to form an array of mutually slit-shaped openings, configured to be placed at a right angle to the beam line, so as to allow the passage of prompt gammas from the target, the collimator being defined at least by three geometrical parameters being the width and depth of the slit-shaped openings and a fill factor. The disclosure is also related to a method for charged hadron therapy verification with a multi-slit camera.

WO 2015/040225 A1 discloses a device and a method for the monitoring of the range of a particle radiation of a cyclotron as radiation device for radiation therapy with at least one detector being able to detect single gamma particles and at least one analyzer. When detecting a gamma particle (event), a signal is created in the detector, whereby the signal is correlated in time with the arrival of the gamma particle in the detector. The analyzer analyzing the signal of the detector assigns a time of detection to either every event or to selected events. The radiation device or a separate particle detector provides a reference signal which is correlated to the emersion of single particles or particle bunches from the radiation device with an uncertainty in time of ≤10 ns. The technique which is also known as prompt-gamma timing (PGT) correlates a time difference between the arrival of the incident protons in the entrance plane of the target and the time of detection of the prompt gamma at the gamma detector. Prompt gamma from protons which travel further in the target are detected later than those stopping earlier, which results in time distribution shifts that can be correlated with the proton range.

WO 2017/156113 A1 discloses techniques for imaging radioactive emission in a target volume include receiving data indicating a set of one or more known emission energies associated with a high energy particle source and determining a Compton line for each emission energy in the set. A Compton camera collects location and deposited energy from an interaction associated with a single source event from a target volume of a subject. For the single source event, an earliest deposited energy, $E_1$, and first scattering angle, $\theta_1$, and a cone of possible locations for the source event are determined. A particular location for the high energy particle source within the target volume without including the single source event, if $E_1$ is not within a predetermined interval of the Compton line for at least one of known emission energies. A solution is presented on a display device.

WO 2012/011083 A1 discloses a device for monitoring photon radiation therapy which comprises a radiation detector plus a multi-hole collimator, readout electronics and a data acquisition system able to process detected events and beam positions, supported by a fixed or telescopic arm attached to the LINAC support structure, or by an independent support. Between the LINAC head and the said collimator a radiation-absorber material can be placed. Also, next to said device, between it and the LINAC head a shielding material can be used. The multi-hole collimator allows for photons escaping the target/patient on a couch to be collected only if they are emitted approximately perpendicular to the central axis of the beam direction.

EP 2 078 537 A1 discloses a radiotherapy treatment support apparatus that includes a storage unit which stores absorption dose volume data expressing a spatial distribution of absorption dose in a subject, a generation unit which generates fusion data associated with morphology volume data of the subject and the absorption dose volume data so as to be associated with a plurality of segments, and a display unit which displays an image which has the distribution of absorption dose superimposed on the two-dimensional morphology image of the subject using the fusion data.

US 2006/0113482 A1 discloses an image-guided radiotherapy apparatus and method in which a radiotherapy radiation source and a gamma ray photon imaging device are positioned with respect to a patient area so that a patient can be treated by a beam emitted from the radiotherapy apparatus and can have images taken by the gamma ray photon imaging device. Radiotherapy treatment and imaging can be performed substantially simultaneously and/or can be performed without moving the patient in some embodiments. The gamma ray photon imaging device can be coupled and movable with respect to any part of a building structure, can be located on a portable frame movable to and from the radiotherapy radiation source and patient, or can take other forms. In some embodiments, the gamma ray photon imaging device can be used for imaging in connection with other types of medical interventions.

EP 2 950 119 A1 discloses a particle beam system for delivering particles or bunches of particles to a target whereby the system is comprising detectors for detecting prompt gammas. Prompt gammas are detected at two different locations with respect to the target and in synchrony with a reference timing signal so as to obtain prompt gamma timing profiles. The difference in time width of the two timing profiles is used to deduce a penetration depth of the particle beam in the target. Further, it discloses a method for verifying a penetration depth of an energetic particle beam by correlating the difference of the two prompt gamma timing profiles with the difference in location of the detectors with respect to the target.

WO 2012/152938 A2 discloses a method and apparatus for verifying the beam range in a target irradiated with a charged hadron beam, such as a proton beam. The beam range is the location of the Bragg peak in the target, being the location where the largest portion of the dose is delivered. The method utilizes a prompt gamma camera provided with a slit-shaped opening, so as to be able to produce a 1-dimensional profile of the dose distribution along the beam line. The camera is mounted with the slit oriented perpendicularly to the beam line. The method comprises the steps of calculating a position of the camera with respect to a target, for a plurality of beam energies and spots to be irradiated. The method further comprises the steps of verifying the beam range for said plurality of spots, and delivering a value representative of the difference between the estimated beam range and the actual beam range. The apparatus is provided with a positioning module for positioning the camera.

JP 2010 032451 A discloses means for confirming the irradiation positions of particle beams with one sort of equipment in a particle beam irradiation system which enables the application of two or more types of particle beams. The system includes a particle beam generator to generate two or more kinds of particle beams, irradiation equipment to emit particle beams onto an object to be irradiated, gamma-ray detectors to detect the gamma rays generated from the object to be irradiated on the basis of the particle beams emitted from the irradiation equipment, a signal processor to determine whether gamma-ray detection signals from the gamma-ray detectors arise from prompt gamma rays or pair annihilation gamma rays, and an irradiation field confirmation device which finds a field irradiated with the particle beams from the gamma-ray detection signals determined to arise from the prompt gamma rays by the signal processor and obtains a field irradiated with the particle beams from the gamma-ray detection signals determined to stem from the pair annihilation gamma rays.

WO 2012/104416 A1 discloses an apparatus and method for charged hadron therapy verification by detecting and/or quantifying prompt gammas produced when irradiating a target with a charged hadron beam. The apparatus comprises a collimator provided with a slit-shaped portion configured to be arranged perpendicularly to the beam line and facing the target, detection means suitable for detecting said prompt gammas and calculation and representation means. In the apparatus and method, the slit is configured to allow the passage of prompt gammas emitted from a range of depths in said target, said depths being measured in the direction of the charged hadron beam. Furthermore, said detection means is configured to detect prompt gammas emitted from each location within said range, and said calculation and representation means is configured to derive from a detected prompt gamma a value representative of the dose at the location from where said prompt gamma is emitted, and to represent a dose-related distribution for a plurality of locations within said range.

PROBLEM TO BE SOLVED

It is therefore an objective of the present invention to provide a device and a method for monitoring a treatment of a body part of a patient with a beam comprising particles, which at least partially avoid the disadvantages of known devices and methods.

Hereby, it is a particular objective of the present invention to provide a device and a method for monitoring the treatment of the body part of the patient which allows a higher resolution in determining the Bragg peak for verifying a range and a dose delivery of the particles provided by the beam to the body part of the patient.

Specifically, it is desired that the device and the method may be designed for considering non-isotropic portions of the prompt-gamma radiation and fragments occurring after the Bragg peak in beam direction in verifying the range and the dose delivery.

SUMMARY OF THE INVENTION

This problem is solved by a device and a method for monitoring a treatment of a body part of a patient with a beam comprising particles as well as a computer program product comprising executable instructions for performing the method according to the subject-matter of the independent claims. Preferred embodiments of the invention, which may be realized in an isolated way or in any arbitrary combination, are disclosed in the dependent claims.

As used in the present specification, the term "comprising" or grammatical variations thereof, are to be taken to specify the presence of stated features, integers, steps or components or groups thereof, but do not preclude the presence or addition of one or more other features, integers, steps, components or groups thereof. The same applies to the term "having" or grammatical variations thereof, which is used as a synonym for the term "comprising".

In a first aspect of the present invention, a device for monitoring a treatment of a body part of a patient with a beam comprising particles is disclosed, wherein the detector comprises:

a beam delivering unit designated for delivering a beam comprising particles and adjusting a direction of propagation of the beam onto a body part of a patient; and a verification unit designated for verifying a range and a dose delivery of the particles provided by the beam to the body part of the patient by determining information about prompt-gamma radiation generated by an interaction of the particles with the body part of the patient at at least two individual interaction points, wherein the verification unit comprises a symmetry axis which is symmetrical with respect to the at least two individual interaction points and which is located perpendicular with respect to the direction of the propagation of the beam.

Accordingly, the device for monitoring the treatment of a body part of a patient may, preferably, be used for monitoring particle therapy of a body part of a patient, wherein the body part of the patient comprises a tumorous tissue. Herein, the tumorous tissue may comprise a tumorous modification which may have been introduced into the tissue of the patient by cancer. As generally used, the term "cancer" refers to a disease of an animal, in particular of a mammal and, especially, of a human, which is characterized by an uncontrolled growth by a group of body cells, usually denoted as "cancer cells". This uncontrolled growth may be accompanied by intrusion into and destruction of surrounding tissue (i.e. "invasion") and possibly spread of cancer cells to other locations in the body (i.e. "metastasis"). Preferably, the cancer may be selected from the list consisting of: acute lymphoblastic leukemia, acute myeloid leukemia, adrenocortical carcinoma, aids-related lymphoma, anal cancer, appendix cancer, astrocytoma, atypical teratoid, basal cell carcinoma, bile duct cancer, bladder cancer, brain stem glioma, breast cancer, burkitt lymphoma, carcinoid tumor, cerebellar astrocytoma, cervical cancer, chordoma, chronic lymphocytic leukemia, chronic myelogenous leukemia, colon cancer, colorectal cancer, craniopharyngioma, endometrial cancer, ependymoblastoma, ependymoma, esophageal cancer, extracranial germ cell tumor, extragonadal germ cell tumor, extrahepatic bile duct cancer, gallbladder cancer, gastric cancer, gastrointestinal stromal tumor, gestational trophoblastic tumor, hairy cell leukemia, head and neck cancer, hepatocellular cancer, hodgkin lymphoma, hypopharyngeal cancer, hypothalamic and visual pathway glioma, intraocular melanoma, kaposi sarcoma, laryngeal cancer, medulloblastoma, medulloepithelioma, melanoma, merkel cell carcinoma, mesothelioma, mouth cancer, multiple endocrine neoplasia syndrome, multiple myeloma, mycosis fungoides, nasal cavity and paranasal sinus cancer, nasopharyngeal cancer, neuroblastoma, nonhodgkin lymphoma, non-small cell lung cancer, oral cancer, oropharyngeal cancer, osteosarcoma, ovarian cancer, ovarian epithelial cancer, ovarian germ cell tumor, ovarian low malignant potential tumor, pancreatic cancer, papillo-matosis, paranasal sinus and nasal cavity cancer, parathyroid cancer, penile cancer, pharynx-geal cancer, pheochromocytoma, pituitary tumor, pleuropulmonary blastoma, primary central nervous system lymphoma, prostate cancer, rectal cancer, renal cell cancer, retinoblastoma, rhabdomyosarcoma, salivary gland cancer, sézary syndrome, small cell lung cancer, small intestine cancer, soft tissue sarcoma, squamous cell carcinoma, squamous neck cancer, testi-cular cancer, throat cancer, thymic carcinoma, thymoma, thyroid cancer, urethral cancer, uterine sarcoma, vaginal cancer, vulvar cancer, waldenström macroglubulinemia, and wilms tumor.

Alternatively or in addition, the device for monitoring a treatment of a body part of a patient may also be used for determining a presence and/or an elemental composition within the body part of the patient that is being irradiated by the particles provided by the beam. Consequently, the term "body part of the patient" includes, in accordance with the present invention, on one hand, a tissue which has been developed within the body of the patient, specifically a tumorous tissue which has been generated within a particular body part as described above, but, on the other hand, also an insert which has been, deliberately or accidentally, introduced into the particular body part of the patient. By way of example, investigating the body composition of a patient may relate to total body nitrogen as a direct measure of total body protein to assess nutritional status. It may also be used to detect early cases of cadmium poisoning in the liver and kidneys in certain polluted areas. Further, total body hydrogen, total body chlorine, and total body calcium are also possible to measure, for which purpose a through in-vivo activation analysis (IVAA) may be employed. By way of a further example, determining the elemental composition of an irradiated target may be used for calculating oxygen and/or carbon concentration of irradiated tumorous tissues, whereby different types of cancer may be detected by their variation in the oxygen and/or carbon concentration. By way of a further example, the insert may be or comprise an implant which has, mainly for medical purposes, been introduced into the body of the patient by an operation. As a further example, the insert may be introduced into the body of the patient as result of accident or a damage. Thus, the device according to the present invention may also be used for determining the presence and/or the elemental composition of an insert, such as a metallic implant, within the body of the patient, in particular in an arrangement in which the metallic implants may be close to the target volume for irradiation. As a result, the term "treatment" refers, on one hand, to a radiotherapy application, specifically for treating the cancer within the tumorous tissue, but, on the other hand, may also refer to determining the presence and/or the elemental composition of an insert, such as an implant, within the body of the patient by treating this particular body part with the particle beam. Further, the term "patient" refers, on one hand, to any person who undergoes the treatment involving the particle beam in accordance with the present invention whether the person requires some kind of medical treatment or not and, on the other hand, to a phantom, specifically to an anthropomorphic phantom. Herein, neutrons, protons or light ions may excite nitrogen, carbon and/or oxygen atoms from the human body which may decay by an emission of prompt-gamma radiation. Herein, low energy lines being associated to the implants may be used as means for investigating the presence of metals or other high-Z materials, whereby the composition of the irradiated target can be assessed in a non-invasive manner. By way of example, in prostate cancer where an implant may be inserted in the rectum in order to provide information whether this organ may be being irradiated or not. Herein, the rectum is sensitive to radiation but close by to the prostate such that sparing it from radiation is desirable for a patient.

As indicated above, the present device is used in situations in which the body part of the patient undergoes a treatment involving a beam comprising particles. As used herein, the term "beam" refers to a plurality of particles which are emitted into a specific direction, by which emission they form a direction of the propagation of the beam, also abbreviated to "propagation direction" of the beam. Further, the beam may be a bundle comprising the particles and having a predetermined extension in a direction which is perpendicular to the propagation direction.

According to the present invention, the device comprises a beam delivering unit. The term "beam delivering unit" refers to an apparatus which is designated for a purpose of delivering the beam and adjusting the propagation direction of the beam onto a body part of a patient. For this purpose, the beam delivering unit may, preferably, comprise a reception for an incident particle beam being provided by a radiation source and an adjustable delivery nozzle being designated for shaping the incident particle beam in a fashion that it may conform to a stereometry of the body part of the patient to be irradiated as far as possible, preferably, with respect to both a cross-sectional shape of the body part and a shape of a distal surface thereof. For this purpose, the beam delivering unit may, further, comprise at least one of a range modulator, a degrader, a collimator or a compensator. However, other kinds of embodiments of the beam delivering unit may also be conceivable.

According to the present invention, the beam comprises hadron particles which are selected from neutrons or ions which propagate along the direction of the beam. Specifically, the ions which are, preferably, used herein are selected from protons $^1$p or from ions of helium $^4$He, of carbon $^{12}$C or of oxygen $^{16}$O, in particular, since each of these kinds or types of ions has a high clinical potential in terms of efficacy and effectiveness. Hereby, carbon ions $^{12}$C are, especially, preferred since they exhibit reduced lateral spread and increased biological effect. The ions which are used for the present invention may, preferably, be provided by a radiation source selected from a cyclotron or a synchrotron in which the particles are accelerated by using a combination of electric fields and magnetic fields. While the particles in the cyclotron travel in a spiral due to a constant applied magnetic field, the magnetic field in the synchrotron is continuously adjusted in a manner that allows keeping the accelerated particles in a circular orbit, resulting in a fixed closed-loop path for the particles. A portion of the particles that are provided in this fashion are, then, used for generating the desired ion beams which travel in one or more beamlines.

As further already indicated above, it is desirable to avoid that healthy organs of the patient receive particles that are provided by the beam as far as possible. For this purpose, the device according to the present invention is designated for monitoring the treatment of the body part of the patient with the particle beam. As generally used, the term "monitoring" refers to a process of continuously acquiring data and deriving desired information therefrom. For this purpose, a plurality of measurement signals may be generated and evaluated, wherefrom the desired information can be determined. Herein, the plurality of measurement signals may be recorded within fixed or variable time intervals or, alternatively or in addition, at an occurrence of at least one prespecified event. In particular, the device according to the present invention may, especially, be designated for continuously determining the particle range in the body part of the patient and the dose delivery into the body part of the patient.

Based on the monitoring, a verification of the range and the dose delivery of the particles provided by the particle beam to the body part of the patient can be performed. As generally used, the terms "verification" and "verifying" relate to providing evidence with respect to the particle range in the body part of the patient and the dose delivery into the body part of the patient, specifically, with respect to a location of the so-called "Bragg peak" within the body part of the patient. As indicated above, the term "Bragg peak" refers to a pronounced peak within a so-denominated "Bragg curve" which denotes a graphical representation of the energy loss of the incident beam with regard to a traveling distance of the beam through the body part of the patient. Advantageously, the Bragg peak occurs immediately before the particles provided by the beam come to rest within the body part of the patient. Herein, the term "range" refers to the traveling distance of the particle within the body part of the patient which is mainly determined by the Bragg peak while the term "dose delivery" relates to an intensity of the particle radiation at the Bragg peak. Thus, the verification is capable of reducing range uncertainties and safety margins during treatment of the patient for significantly reducing side effects to the patient by preventing the healthy organs of the patient from receiving radiation.

Further, the device according to the present invention comprises a verification unit. As used herein, the term "verification unit" relates to an apparatus which is designated for verifying the range and the dose delivery of the particles which are provided by the beam to the body part of the patient. For this purpose, the verification unit is adapted for determining information about prompt-gamma radiation which is generated by an interaction of the particles with the irradiated body part of the patient. As generally used, the term "interaction" refers to a response which is provided by the body part of the patient upon irradiation by the particles. As further generally used, the term "prompt-gamma radiation" refers to secondary radiation emission which is induced by nuclear reactions in correlation to the path of the particles in matter. For this purpose, the energy of the particles being provided by the incident beam are absorbed inside the body part of the patient. Thus, the prompt-gamma radiation generated in this manner can be used according to the present invention for verification, preferably for real-time verification, of the particle range within the body part of the patient and the dose delivery into the body part of the patient under clinical conditions, which may, preferably result in reducing uncertainties in treatment planning.

According to the present invention, the treatment of the body part of the patient with the particle beam is monitored by determining the information about the prompt-gamma radiation at at least two individual interaction points, preferably at two, four, six, eight, twelve, or more different interaction points, wherein two, four, six, eight or twelve interaction points are preferred. In general, the number of interaction points to be selected for monitoring purposes may be adjusted in order to achieve sufficient information having high spatial resolution by reducing any effort as far as possible. As used herein, the term "interaction point" refers to a location in the body part of the patient at which the particular response of the body part of the patient upon its irradiation by the particles which can observed by the verification unit takes place. As indicated above, the prompt-gamma radiation is not isotropic but rather involves a higher yield with respect to backward-peaked and forward-peaked gamma radiation. Further, the desired range verification turned out to be more complex due to a presence of fragments which occur after the Bragg peak in beam direction. Consequently, determining the prompt-gamma radiation at at least two individual interaction points of the particles with the body part of the patient allows increasing an accuracy of the verification of the particle range within the Bragg peak compared to other devices and methods according to the state of the art.

In accordance with the present invention, the verification unit comprises a symmetry axis, wherein the symmetry axis is symmetrical with respect to the individual interaction points. As generally used, the term "symmetry axis" relates to a set-up and an arrangement of the verification unit in which two halves of the verification unit being generated by the symmetry axis are identical with respect to each other, in particular, in a fashion that one half looks like an image of the other half as in a mirror. Herein, the two halves can, physically, be present in the verification unit in a simultaneous manner, such as by a symmetrical arrangement of respective detector elements. As described below in more detail, in an alternative embodiment in which only a single detector element may, physically, be present in the verification unit, the single detector element may be movable within the verification unit to symmetrical positions with regard to individual interaction points.

In further accordance with the present invention, the symmetry axis of the verification unit is located in a perpendicular manner with respect to the direction of the propagation of the beam. As used herein, the term "perpendicular" refers to an angle of $90°\pm10°$, preferably of $90°\pm1°$, preferably of $90°\pm0.1°$, with respect to the propagation direction of the beam. Similarly, the term "parallel" relates to an angle of $0°\pm10°$, preferably of $0°\pm1°$, preferably of $0°\pm0.1°$, with respect to the propagation direction of the beam. Thus, the information about the prompt-gamma radiation which is determined by the verification unit only comprises components which are perpendicular to the propagation direction of the beam.

As a consequence of the perpendicular arrangement of the symmetry axis of the verification unit with respect to the direction of the propagation of the beam, at least one plane may be formed, wherein at least two of the detector elements of the verification unit may be located in a symmetrical manner or wherein, in the alternative embodiment as indicated above, the single detector element of the verification unit may be moveable in a symmetrical fashion. In a case in which the verification unit may comprise four, six, or more detector elements, two of the detector elements which may be located in a symmetrical manner may form an individual plane. However, irrespective of the number of the detector elements within the plane, each plane may intersect the direction of the propagation of the beam. In order words, the plane comprises a straight line along the direction of the beam and one of a multitude of possible points from the detector element, such that all detected prompt-gamma lies within this plane.

Further an "emission angle" may be defined by an origin of the prompt-gamma ray at a particular interaction point along the direction of the beam and a point of detection by the respective detector element. Since all detected prompt-gamma lies within the above-defined plane, the emission angle may rotate on the plane around the interaction point which is the origin of the prompt-gamma ray to be detected. A reconstruction of a detection line within the body part of the patient and the at least one detector element comprises a knowledge of the location of the at least one detection point and the straight line as defined by the beam direction. In other words, intersecting the detection line with the direction of the propagation of the beam, the interaction point can be detected. As a result of the arrangement according to the present invention, the several emission angles are located within the plane in a co-planar fashion. A different plane which may not cross the straight line and the detection point is not relevant. Consequently, for each prompt-gamma radiation as generated by the interaction of the beam with the body part of the patient, the origin of the prompt-gamma radiation may be associated to the place where the interaction took place. At this location, the beam may exhibit a specific energy which decreases with increasing depth of the beam in the body part of the patient. As a further result, an angular cross-section may depend on the emission angle as shown by Rusiecka et al and Kiener, see above, wherein certain emission angles may exhibit higher cross-sections than other emission angles, resulting in an expectation of a higher prompt-gamma yield for certain emission angles compared to other emission angles.

As a further consequence of the perpendicular arrangement of the symmetry axis of the verification unit with respect to the direction of the propagation of the beam, the verification unit is designated for moving perpendicular to the propagation direction of the beam within the at least one plane formed by the detector elements and the direction of propagation of the beam, thus, being especially designed for acquiring information about the prompt-gamma radiation being generated as secondary radiation emission by an interaction of the particles with the body part of the patient at at least two individual interaction points of the particles impinging the body part of the patient.

As a particularly significant result of using the at least two individual interaction points for the monitoring of the treatment of the body part of the patient with the particle beam, the device and the method according to the present invention are designed for determining absolute values for the particle range within the body part of the patient. Herein, the term "absolute value" refers to a piece of data which is provided in a form of a number and a physical unit, wherein the physical unit, specifically, refers to a distance, such as given in μm, within the body part of the patient. This feature is in contrast to known devices and methods which are only capable of providing the particle range in form of relative values, wherein the term "relative values" refers to a further piece of data which is provided in a form of a number only or of a number and an arbitrary unit which is not in a relationship with a physical unit, such as the distance, inside the body part of the patient. As a result of determining absolute values for the particle range, distances within the body part of the patient can be determined with a high spatial resolution, thereby, allowing a confinement of the treatment of the body part of the patient by the incident particle beam to the desired particle range, in particular to the tumorous tissue comprising the tumorous modification introduced by cancer.

In accordance with to the present invention, the perpendicular arrangement of the symmetry axis of the verification unit with respect to the direction of the propagation of the beam may be provided in form of various embodiments.

In a preferred embodiment, the device further comprises a single rotational gantry and a patient positioning platform, wherein at least one of the gantry and a patient positioning platform is movable with respect to the other in a fashion that the direction of the propagation of the beam is adjustable to different positions with respect to the patient. As generally used, the term "movable" refers to a feature of a part which indicates that the location of the respective part is not fixed such that the part can be brought to a different location. This kind of configuration may allow amending a distance and/or a relative orientation between the gantry and a patient positioning platform already by moving only a single part of the device.

As further generally used, the term "patient positioning platform" refers to a reception which is designated for receiving the patient, for moving the patient into an appropriate position designated for receiving the treatment, and for maintaining the patient in this position during the treatment. For this purpose, robotic instrumentation may, preferably, be employed for accurately positioning the patient with regard to six directions of movement or rotation. However, further kinds of patient positioning platforms may also be feasible. Since the patient is, usually, a human person who exhibits a geometry having a rotational symmetry along a longitudinal axis, the patient positioning platform may, preferably, be designed in order to reflect this geometry of the patient. As a result of this configuration, the patient positioning platform may comprise a platform having an elongated shape which may, preferably, be adapted to the longitudinal axis of the patient. Moreover, the elongated shape of the patient positioning platform may be used for defining a "plane" of the patient positioning platform, such as by employing an adjustment function, such as a fit function.

As further generally used, the terms "rotational gantry" or simply "gantry" refer to a unit which is adapted to receive the patient positioning platform and to be rotated, preferably over a full circle of 360°, with respect to the patient positioning platform in order to deliver the particle beam to the body part of the patient at any desired angle, specifically at an angle which may be specified by the treatment. In accordance with this embodiment, the gantry, the patient positioning platform, or both the gantry and the patient positioning platform may be designated to be moved in order to adjust the propagation direction of the particles with respect to the patient as desired.

In this preferred embodiment, the gantry may comprise a moveable side wall and a moveable front wall, wherein the front wall may be placed perpendicular with respect to the side wall. As used herein, the term "side wall" refers to a first portion of an inner surface of the gantry which is located parallel with respect to the longitudinal axis of the patient whereas the term "front wall" refers to a further portion of the inner surface of the gantry which is located perpendicular with respect to the longitudinal axis of the patient. Further, a remaining portion of the gantry may be open for access of the patient positioning platform by the patient, by medical personnel, or by service personnel. As a result of this embodiment, the front wall may assume a perpendicular orientation with respect to the side wall. However, other kinds of embodiments for the gantry as well as further arrangements which may relate to different directions and/or orientations of the patient positioning platform inside the gantry can also be feasible.

In a particular embodiment, both the beam delivering unit and the verification unit may be coupled to the side wall and movable with the side wall to different positions with respect to the patient positioning platform in a synchronized manner. As used herein, the term "synchronized" refers to a fashion of movement of at least two individual parts, wherein the individual parts are moved with an identical direction vector and an identical rotation vector, wherein each one of the direction vector or the rotation vector can be a zero vector. As result of this embodiment, the perpendicular arrangement of the symmetry axis of the verification unit with respect to the propagation direction of the beam can be maintained during the treatment although only the side wall can be moved while other parts of the device, such as the front wall or the patient positioning platform, may be maintained in position.

In an alternative embodiment, the beam delivering unit may be coupled to the side wall and be movable with the side wall to different positions with respect to the patient positioning platform whereas the verification unit may be coupled to the front wall and be movable with the front wall to different positions with respect to the patient positioning platform in a synchronized manner with the beam delivering unit. As already indicated above, the front wall may, preferably, assume a perpendicular orientation with respect to the side wall such that, in this configuration, the perpendicular arrangement of the verification unit with respect to the direction of the propagation of the beam can be maintained during the treatment in a particularly easy fashion.

In a further alternative embodiment, the beam delivering unit may be provided in a fixed position with respect to the patient positioning platform, wherein the beam delivering unit may be designated for delivering the beam in any orientation with respect to the patient positioning platform, preferably at an angle of 0° or 90°. Alternatively, the beam delivering unit may be designated for delivering the beam at an angle of 45°±45°. Thus, the beam delivering unit may be provided in a vertical orientation or a nearly vertical orientation with respect to the plane as defined by the patient positioning platform while the verification unit may be provided in a perpendicular orientation thereto in order to avoid interference with movements of the patient positioning platform, preferably at an angle of 45°, or it may be movable around the patient positioning platform to the desired position in order to avoid a conflict with the patient positioning platform. As result of this configuration, the verification unit can always maintain the desired perpendicular orientation with respect to the direction of the propagation of the beam irrespective of a movement of the beam delivery unit.

In a further alternative embodiment, a toroidal gantry, such as disclosed in WO 2019/224215 A1, may be used, wherein the gantry does not rotate. Herein, the beam has various possible directions and the magnetic field is zero inside the torus. The device according to the present invention could, however, be used by rotating independently of the gantry but, still, being perpendicular to the direction of the beam. Herein, synchronization of the device could be provided by using prior information related to the direction of the beam, wherein the at least one detector element is not synchronized with the gantry but with the direction of the beam. As an alternative, an independent device could be attached to possible delivery angles of the beam.

In the following, further preferred embodiments of the invention which may be realized in an isolated way or in any arbitrary combination are disclosed in more detail.

In a particularly preferred embodiment, the verification unit may comprise at least one detector element, wherein the detector element is designated for determining the prompt-gamma radiation as generated by the interaction of the particles with the body part of the patient.

As used herein, the term "detector element" refers to an apparatus which is designated for generating a measurable signal from the incident prompt-gamma radiation. For this purpose, the measurable signal may, preferably, be selected from an electrical signal, specifically an electrical voltage or an electrical current. In particular, the detector element may be selected from at least one of: a photomultiplier tube (PMT), a solid-state single-photon-sensitive device (silicon photomultiplier; SiPM), a charge-coupled device (CCD), a complementary metal-oxide-semiconductor (CMOS), or a quanta image sensor (QIS) chip. However, other kinds of detector elements may also be feasible. In case the verification unit may comprise more than a single individual detector element, it is particularly preferred that the individual detector elements are of the same type and kind in order to increase a comparability of the measured signals between the individual detector elements.

In this particularly preferred embodiment, the verification unit may comprise at least two detector elements, preferably two, four, six, eight, twelve, or more detector elements. Herein, the two detector elements are spaced apart with respect to each other and are, thus, capable of determining the information about the prompt-gamma radiation at the at least two individual interaction points, preferably in a simultaneous manner. However, consecutively determining the information about the prompt-gamma radiation may, alternatively or in addition, also be feasible.

Further, each detector element may, preferably, be designated for being movable towards or away from the body part of the patient in a fashion perpendicular to the propagation direction of the beam, whereby a distance between each detector element and the body part of the patient is maintained equal for each detector element. Maintaining the same distance between each detector element and the body part of the patient allows determining the desired information about the prompt-gamma radiation with the same intensity, thus, increasing the comparability of the measured signals between each detector element. As used herein, the term "towards or away from the body part" relates to a movement which decreases or increases the distance between a particular detector element and the body part of the patient. By moving a particular detector element in this fashion, a distance between two individual interaction points can be adjusted. As a result thereof, a position along the propagation direction of the beam can be focused or defocused, whereby a spatial resolution for the detection of the prompt-gamma radiation may be set in this fashion. For this purpose, each detector element can, in a particular embodiment, be applied to an individual member of a support, wherein the support may be directly coupled to the gantry, such as to the side wall of the gantry, and wherein the at least one individual member can be movable with respect to the gantry in a direction perpendicular to the propagation direction of the beam. In a further configuration, four or more detector elements may be arranged in form of an array. For further details with regard to the detector elements, the support and the individual members of the support, reference may be made to the examples in the description below. However, further kinds of arrangements of the detector elements may also be conceivable.

In an alternative embodiment, the verification unit may comprise only a single detector element. However, in order to be able to, nevertheless, determine the information about the prompt-gamma radiation at the at least two individual interaction points, the single detector element may, preferably, be designated for being placed at at least two different positions within the verification unit with respect to the body part of the patient. During a movement between a placement at the least two different positions the distance between the detector element and the body part of the patient is, preferably, maintained for each different position for the same reason as indicated above. In this alternative embodiment, the single detector element may, thus, move between the at least two different positions at a first time scale which is faster compared to a second time scale of moving the detector element towards or away from the body part of the patient perpendicular to the propagation direction of the beam, whereby the distance between the individual interaction points can be adjusted as further described above. Herein, moving the detector element towards or away from the body part may be associated to iso-energy slices (IES). For every slice, the detector element can be moved to a position according to the desired resolution. Herein, the slice at a most distal end may demand a more focused configuration for higher resolution. By way of example, a delivery time for every slice may be 5 seconds followed by 4 seconds pause between two following slices. In this example, the pause of 4 seconds may constitute the second time scale as defined above, wherein the first time scale of the 5 seconds may be the delivery time which includes the movements between the two different positions of the detector element. In case of multiple IES delivery in order to increase delivery speed, this embodiment could, however, still be used for focusing on the most distal slice. Whereas using a single detector element only may be advantageous for the purpose of quality assurance of the device due to its simplicity, at least two, preferably four, six, eight or twelve detector elements may, particularly, be preferred for an actual treatment of a patient since this configuration may allow increasing a sensitivity of the verification unit and, therefore, a spatial resolution for the determination of the particle range within the body part of the patient.

Further, the verification unit may, further, comprise a collimator unit. As generally used, the term "collimator unit" refers to an apparatus which is designated for collimating and shaping the prompt-gamma radiation after having been generated by the interaction of the particles with the body part of the patient but prior to entering the at least one detector element. Collimating the prompt-gamma radiation prior to its detection in a corresponding detector element may, advantageously, result in a desired increase of spatial resolution of the detection of the prompt-gamma radiation within the body part of the patient. However, a verification unit without a collimator unit may also be conceivable.

In addition, the verification unit may, further, comprise an evaluation device. As generally used, the term "evaluation device" relates to an apparatus which is designated for determining the information about the prompt-gamma radiation which has been acquired by the at least one detector element and which is, specifically, based on the measurable signals being provided by the at least one detector element to the evaluation device. For this purpose, a wire-based connection, or, alternatively or in addition, a wireless connection between the at least one detector element and the evaluation device may be provided.

The evaluation device according to the present invention may, particularly, be designed for verifying the particle range and the dose delivery of the particles as provided by the beam to the body part of the patient, wherein this kind of information may be based on the measurable signals which are provided to the evaluation device by the at least one detector element. For this purpose, the evaluation device may comprise a fast analog-to-digital converter, preferably having a sampling rate of 10 ns, more preferably of 4 ns, more preferably of 1 ns or below. Herein, the fast analog-to-digital converter may, preferably, be selected from at least one of: a flash analog-to-digital converter (FADC), a field-programmable gate array (FPGA), a versa module eurocard (VME) digitizer, a time readout board (TRB), or an oscilloscope. However, other types of fast analog-to-digital converter may also be conceivable.

In a further aspect of the present invention, a method for monitoring a treatment of a body part of a patient with a beam comprising particles is disclosed. Herein, the method according to the present invention comprises at least the following steps, wherein, however, additional steps may further be performed. In a preferred embodiment, the indicated steps may be performed in a sequential approach, wherein, however, a subsequent step may at least partially be performed concurrently with a previous step. In an alternatively preferred embodiment, the mentioned steps may be performed in an integrative approach or in a mixed approach combining the sequential approach and the integrative approach, in particular, for minimizing time and/or storing space required for performing the present method. In addition, further steps which are not indicated here may also be performed.

In particular, the method for monitoring a treatment of a body part of a patient with a beam comprising particles comprises the steps of:
  providing a device for monitoring a treatment of a body part of a patient with a beam comprising particles as described elsewhere herein;
  delivering a beam comprising particles and adjusting a direction of propagation of the beam onto a body part of a patient;
  determining information about prompt-gamma radiation generated by an interaction of the particles with the body part of the patient at at least two individual interaction points of the beam comprising the particles with the body part of the patient; and
  verifying a range and a dose delivery of the particles provided by the beam to the body part of the patient.

In a particularly preferred embodiment, determining the information about the prompt-gamma radiation may, preferably, comprise
  specifying at least two positions along the direction of the propagation of the beam by moving at least one detector element comprised by the verification unit perpendicular to the direction of the propagation of the beam;
  moving an individual member of a support further comprised by the verification unit, wherein the at least one detector element is applied to the individual member, wherein the individual member is moved towards or away from the body part of the patient in a manner that the position along the direction of the propagation of the beam is focused or defocused, whereby a spatial resolution for the detection of the prompt-gamma radiation is set; and
  detecting the signal generated by the interaction of the prompt gamma radiation with the at least one detector element.

In this particularly preferred embodiment, determining the information about the prompt-gamma radiation may, preferably, further comprise
  determining a multitude of angular cross-sections between the particles and the body part of the patient, wherein each angular cross-section is determined for a different emission angle of 30° to 150°; and
  evaluating an energy of the beam and of the prompt-gamma radiation generated by the interaction of the particles with the body part of the patient for each interaction point.

In this particularly preferred embodiment, the evaluating of the energy of the beam and of the prompt-gamma radiation for each interaction point may, in particular, comprise
  reconstructing a detection line between the interaction point within the body part of the patient and the at least one detector element;
  intersecting the detection line with the direction of the propagation of the beam, thereby detecting the interaction point; and
  determining a multitude of interaction points with respect to the energy and the angular cross-section, whereby the range and the dose delivery of the particles provided by the beam to the body part of the patient are verified.

In addition to the indicated method steps, further method steps may also be performed, in particular a step of "planning the treatment", which may comprise the following sub-steps:

defining the direction of the propagation of the beam;
defining the at least one body part to be treated by receiving a dose;
defining the at least one further body part to be spared by not receiving a dose; and
defining at least one energy of the beam and a number of particles to be delivered to at least one region within the at least one body part to be treated.

In this preferred embodiment, the delivery of the particles by the beam to the body part of the patient can be corrected if errors may be found between a treatment plan and measurements in accordance with the following further sub-steps:

measuring a range difference and a dose difference between the treatment plan and the data acquired during the treatment with the method and the device according to the present invention;
deciding whether at least one difference may result in a deviation which may be too large such that any further action should be taken;
if the deviations are too large, establishing a new treatment plan using also the information acquired by the method and the device according to the present invention; and
updating the above-indicated step of "delivering a beam comprising particles and adjusting a direction of propagation of the beam onto a body part of a patient".

In a further preferred embodiment of the present invention, a model for determining a prompt-gamma yield with a certain energy may be established for every beam energy and emission angle, wherein the model may, preferably comprise the angular cross-sections between the particles and the body part of the patient, properties of the detector element, relative positions between beam, patient and verification unit, and, optionally, the treatment plan.

In a further aspect, the present invention relates to a method for monitoring a treatment of a body part of a patient with a beam comprising particles as described elsewhere herein. This method may be frequently performed, in particular, during a commissioning of the device or within a regular quality assessment, such as every week, fortnight or month. This method may comprise the following steps:

providing a device for monitoring a treatment of a body part of a patient with a beam comprising particles as described elsewhere herein;
delivering a beam comprising particles and adjusting a direction of propagation of the beam onto a body part of a surrogate phantom;
calculating an energy of the beam at a certain depth within the patient and measuring the energy and yields of the prompt-gamma radiation;
determining a multitude of angular cross-sections for every beam energy, emission angle and prompt gamma yield with a certain energy;
optionally, combining the energy of the beam at a certain depth within the surrogate phantom and the energy of the prompt gamma radiation;
establishing a model for determining the prompt gamma yield with a certain energy for every beam energy and emission angle;
determining a multitude of interaction points with respect to the energy and the angular cross-section, whereby the range and the dose delivery of the particles provided by the beam to the body part of the patient are verified;
comparing the predictions of the model with the results obtained from the measurements of the prompt-gamma radiation; and
verifying a range and a dose delivery of the particles provided by the beam to the body part of the patient.

For further details with respect to the methods, reference may be made to the device for monitoring the treatment of the body part of the patient with the beam comprising the particles according to the present invention as described elsewhere in this document.

In a further aspect, the present invention refers to computer program product which comprises executable instructions for performing the methods as described elsewhere herein. For further details with respect to the computer program product reference may be made to the methods and the device for monitoring a treatment of a body part of a patient with a beam comprising particles according to the present invention as described elsewhere in this document.

The device and the methods according to the present invention provide considerable advantages over known devices and methods. In particular, the device and the method for monitoring a treatment of a body part of a patient with a beam comprising particles is capable of monitoring the treatment of the body part of the patient with a higher resolution for determining the Bragg peak for verifying a range and a dose delivery of the particles provided by the beam to the body part of the patient. Specifically, the device and the method can, advantageously, be used for considering non-isotropic portions of the prompt-gamma radiation and fragments occurring after the Bragg peak in beam direction when verifying the range and the dose delivery. Further, it can be used for determining the elemental composition of an irradiated target. Further, it can be used for tracking high-Z materials within the beam path. Further, it can be used for quality assurance and plan verification before treatment.

The present invention is in particular contrast to US 2006/0113482 A1 which discloses a coupled and movable photon imaging device rotating around a patient, wherein, a portable frame can move to and from the radiotherapy radiation source and the patient in a similar fashion as proposed by Hueso-González et al., see above. In accordance with the present invention, the range of the beam can be controlled in a real-time fashion by measuring the prompt-gamma radiation at various closer or further interaction points along the beam direction. The geometric problems involved are, therefore, different and variables which are used for the respective purposes as well. While their lines-of-response are isotropic and the signal resulting from the positron annihilation in the organs depends on the uptake of that organ, the lines-of-response according to the present invention are related to an emission from the body part of the patient actually being crossed by the beam. Whereas US 2006/0113482 A1 attempts to track or image the patient in an anatomical, morphological and/or functional view in order to adapt the treatment of the patient, tracking and/or imaging of the beam is performed, in accordance with the present invention, for adapting the beam positioning within the body part of the patient.

The present invention is in further particular contrast to EP 2 950 119 A1 which discloses the determination of a photon travel shift instead of a Bragg peak. This photon travel shift is defined as a distance travelled by a photon in a time interval equal to the difference between a first and a second time width. First and second time width are thereby acquired via timing profiles from two detectors scanning an extended special interval instead of individual interaction points. The information obtained from the photon travel shift is then used to calculate the penetration depth in the target but not a delivery dose which depends on further parameters.

The present invention is in further particular contrast to WO 2012/152938 A2 which discloses no symmetry in the detector arrangement and movement, respectively. The concept as proposed therein using slit-camera devices rather relies on an asymmetrical detection of interaction points. The detectors are further relatively thin and cannot absorb the full energy of the prompt gamma radiation so that a plurality of detectors is required to increase the spatial resolution. The slit-cameras are more closely described in WO 2012/104416 A1 which follows the same underlying concept. Also JP 2010 032451 A and Richter et al. do not disclose a corresponding spatial symmetry concerning the detector setup. They further also do not disclose methods for retrieving a delivery dose from prompt-gamma distributions. In this context, Richter et al. only disclose CT based dose reconstructions.

SHORT DESCRIPTION OF THE FIGURES

Further optional details and features of the present invention may be derived from the subsequent description of preferred embodiments, preferably in combination with the dependent claims. Therein, the respective features may be realized in an isolated way or in arbitrary combinations. The invention is not restricted to the preferred embodiments. Identical reference numbers in the figures refer to identical elements or to elements having identical or similar functions or to elements corresponding to each other with regard to their functionality.

Figure 3:
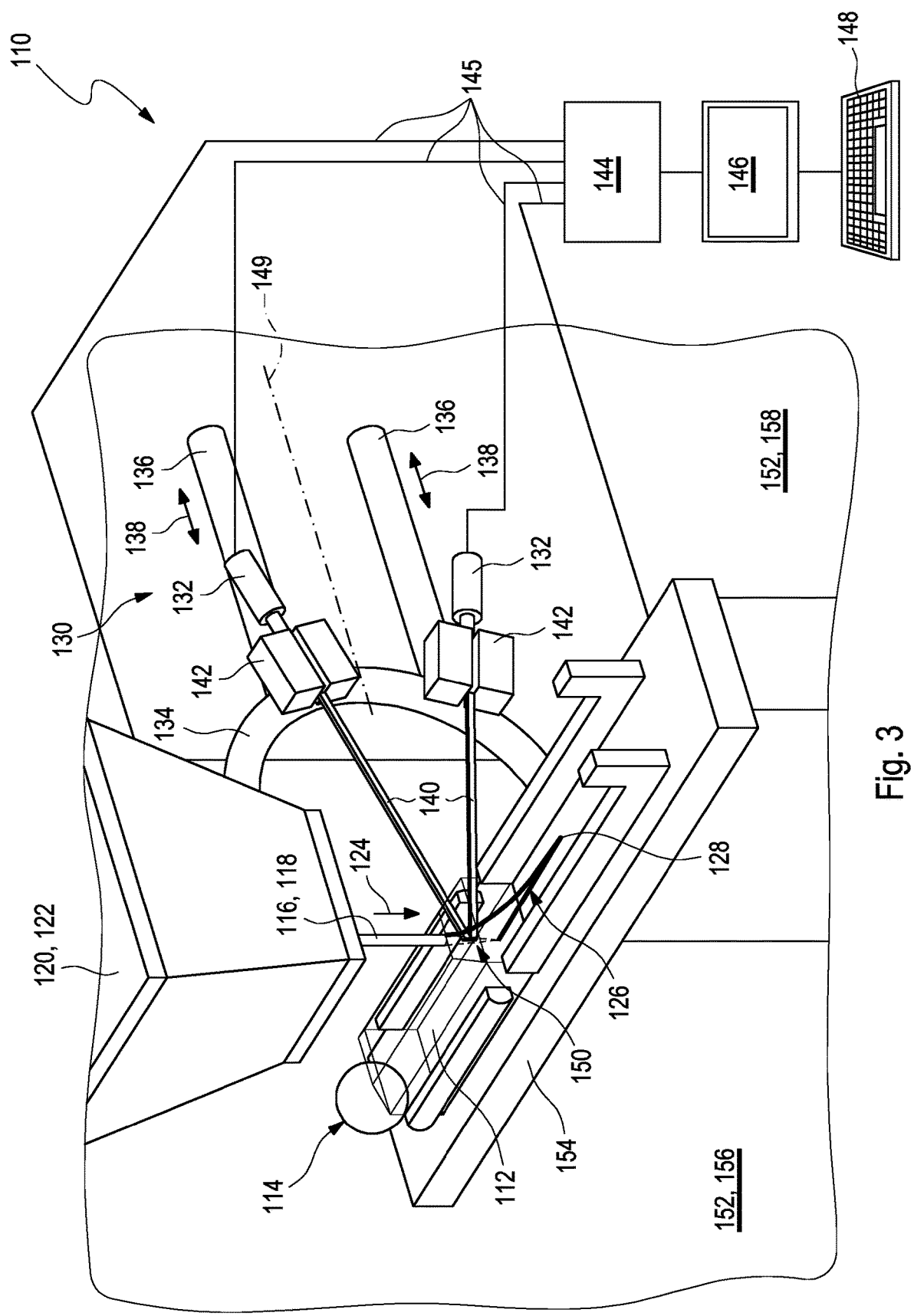
Figure 4:
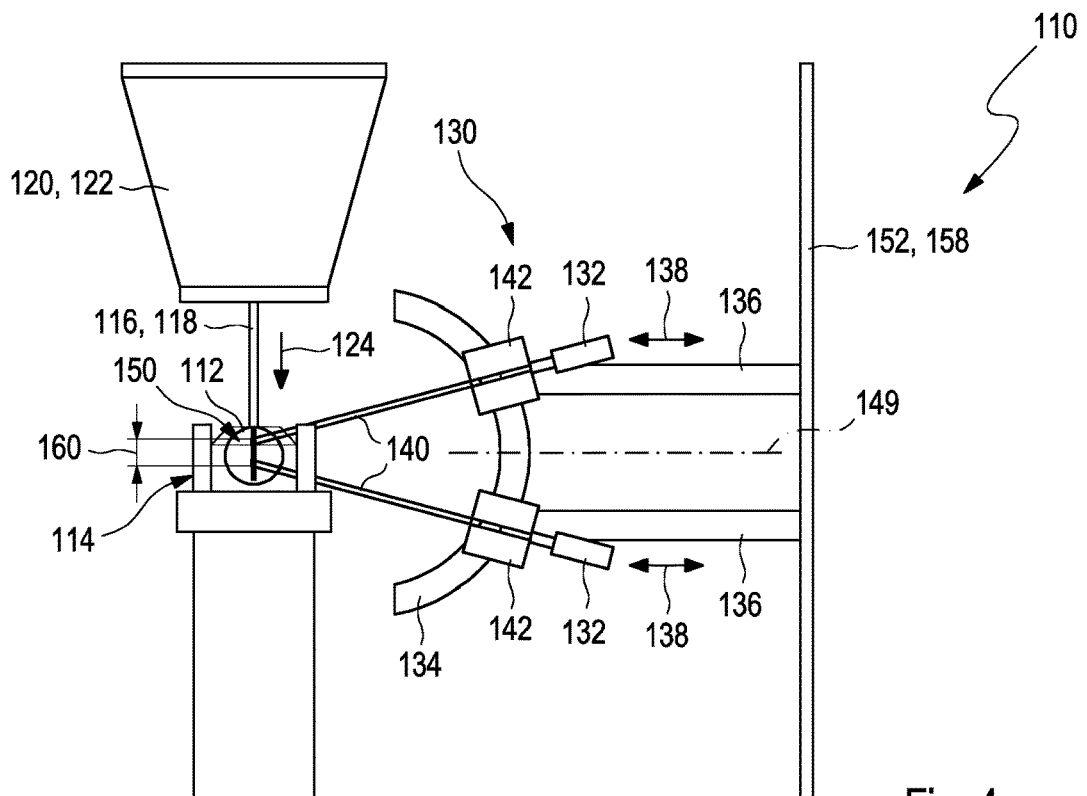
Figure 4:
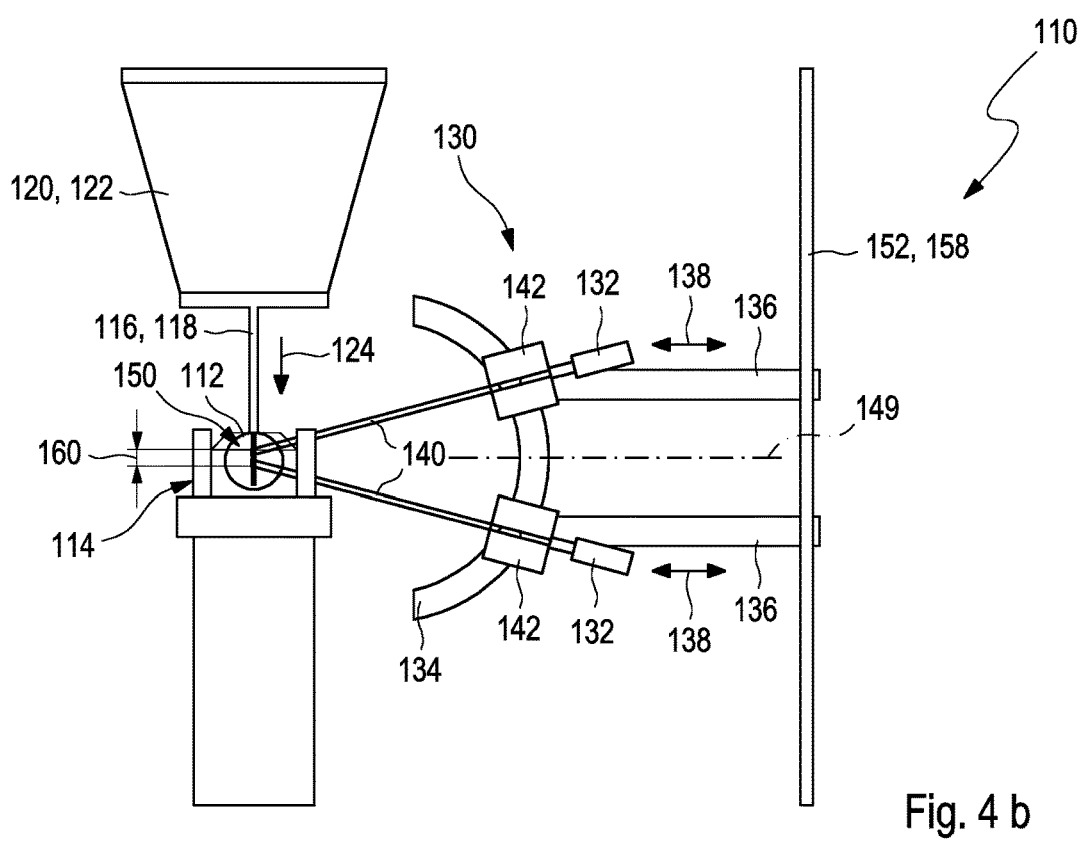

FIG. 3 illustrates a further preferred embodiment of the device for the monitoring of the treatment of the body part of the patient with the particle beam in a perspective view, wherein the device comprises a beam delivery unit in a top arrangement and a verification unit having two individual detector elements; and FIGS. 4A and 4B further illustrate the preferred embodiment of a method for monitoring a treatment of a body part of a patient with a beam comprising particles of FIG. 3 in a side view, wherein the detector elements are moved between FIGS. 4A and 4B for adjusting a distance between two individual interaction points, whereby a spatial resolution for the detection of prompt-gamma radiation is set.

DESCRIPTION OF PREFERRED EMBODIMENTS

Figure 1:
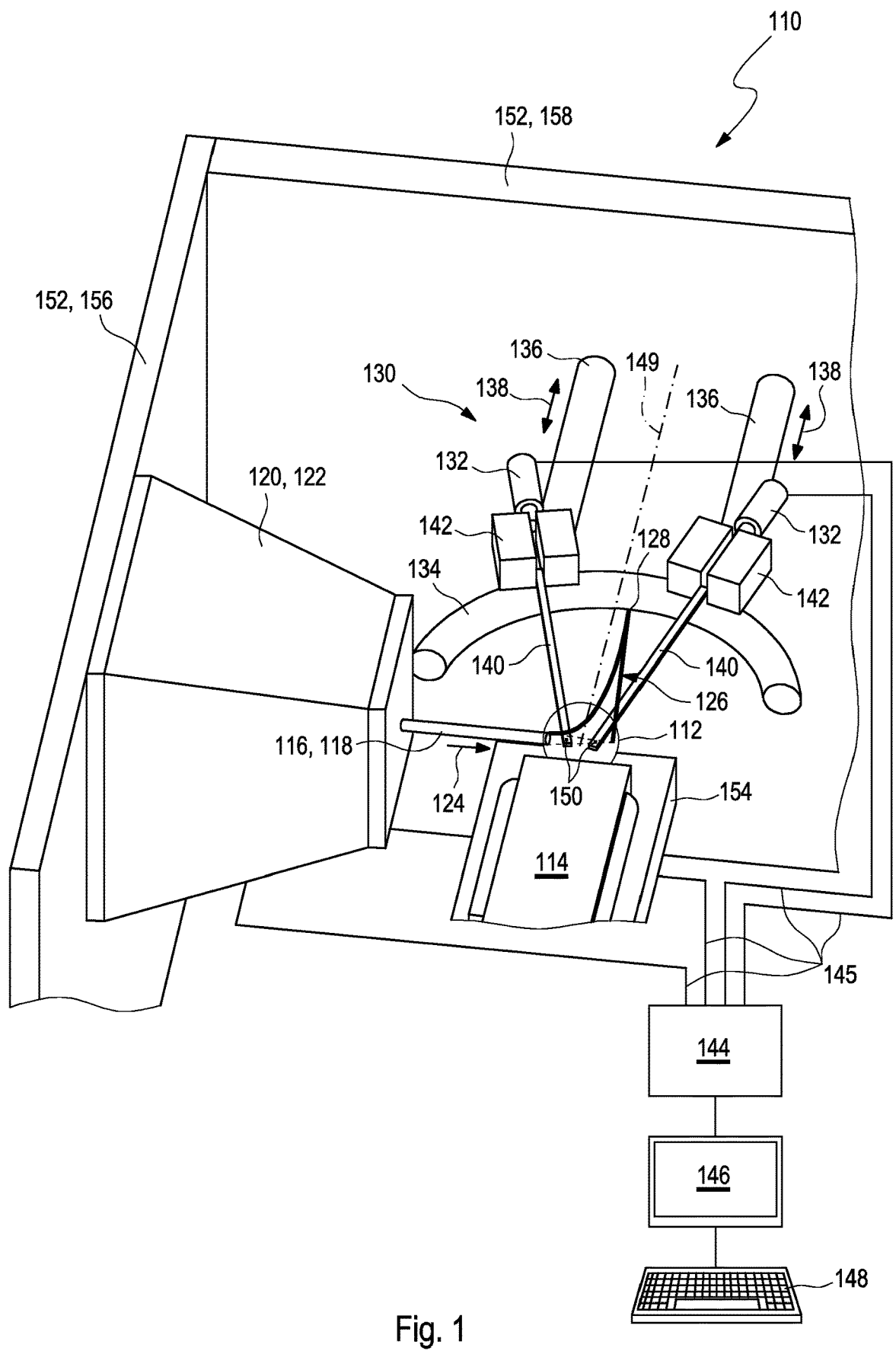
FIG. 1 illustrates a preferred embodiment of a device for monitoring a treatment of a body part of a patient with a particle beam in accordance with the present invention in a top view, wherein the device comprises a beam delivery unit in a side arrangement and a verification unit having two individual detector elements.

FIG. 1 illustrates, in a top view, a preferred embodiment of a device 110 for monitoring a treatment of a body part 112 of a patient 114 with a beam 116 comprising particles 118 in accordance with the present invention. As already indicated above, the particles 118 which are, preferably, used in the context of the present invention are hadrons selected from neutrons $^0$n, protons $^1$p, or from ions of helium $^4$He, of carbon $^{12}$C or of oxygen $^{16}$O, in particular, since these particles 118 exhibit a high clinical potential in terms of efficacy and effectiveness. However, other kinds of particles 118 can still be used by the device 110 of the present invention.

As schematically depicted in FIG. 1, the device 110 comprises a beam delivering unit 120 which is provided here in form of an adjustable delivery nozzle 122. According to the present invention, the beam delivering unit 120 is designed for both delivering the incident beam 116 comprising the particles 118 and, concurrently, for adjusting a direction 124 of a propagation of the beam 116 in a fashion that the particles 118 which are comprised by the beam 116 may actually impinge at the desired body part 112 of the patient 114 which has been selected as a target volume for the particles 118 in order to perform the envisaged treatment. As a result thereof, the beam delivering unit 120, in particular the adjustable delivery nozzle 122, may shape the incident beam 116 in a manner that the beam 116 may conform to a stereometry of the body part 112 to be irradiated as far as possible, specifically with respect to both a cross-sectional shape of the body part 112 and a shape of a distal surface of the body part 112. For this purpose, the beam delivering unit 120 may, further, comprise at least one of a scanning magnet, a range modulator, a degrader, a collimator or a compensator (not depicted here). However, other kinds of arrangements for the beam delivering unit 120 may also be conceivable.

In this respect, FIG. 1 further schematically illustrates a so-called Bragg curve 126 which denotes a graphical representation of an energy loss of the incident beam 116 with respect to a traveling distance of the beam 116 through the irradiated body part 112 of the patient 114. The beam 116 which comprises hadron particles 118 exhibits the advantageous effect that a peak in the Bragg curve 126, which is also denoted as Bragg peak 128, occurs immediately before the hadron particles 118 come to rest. Thus, in order to prevent healthy organs from receiving radiation, it is desirable that the Bragg peak 128 assumes a location which is within the irradiated body part 112 of the patient 114.

In order to solve this problem, the device 110 comprises a verification unit 130 which is designated for verifying a range and a dose delivery of the particles 118 as provided by the beam 116 to the irradiated body part 112 of the patient 116. In the preferred embodiment of FIG. 1A, the verification unit 130 comprises two individual detector elements 132 which are spaced apart with respect to each other and are, thus, capable of determining the information, preferably, in a simultaneous manner. However, consecutively determining the information may, alternatively or in addition, also be feasible. Herein, each detector element 132 is attached to a support 134 having individual members 136 which are movable towards or away from the body part 112 of the patient 114 as indicated by arrows 138, wherein the same distance between each detector element 132 and the body part 112 of the patient 114 is maintained. As described below in more detail in the context of FIGS. 4A and 4B, the individual members 136 can, thus, be moved towards or away from the body part of the patient in order to set a spatial resolution for the individual detector elements 132. It is indicated here that the support 134 and the corresponding individual members 136 may be provided as illustrated or in various kinds of different arrangements or configurations as long as attaching the detector elements 132 and moving the detector elements 132 towards or away from the body part 112 of the patient 114 in the indicated fashion is possible.

For a purpose of verifying the range and the dose delivery of the particles 118 irradiating the body part 112 of the patient 116, the verification unit 130 is adapted for determining information about prompt-gamma radiation 140, wherein the prompt-gamma radiation 140 is generated by an interaction of the particles 118 as provided by the incident beam 116 with the irradiated body part 112 of the patient 114. As already described above, the prompt-gamma radiation 140 refers to secondary radiation emission which is induced by nuclear reactions in correlation to the path of the particles 118 being provided by an energy of the incident beam 116 which is absorbed inside the body part 112 of the patient 114. Thus, the prompt-gamma radiation 140 which is generated in this fashion constitutes an appropriate tool for verification, preferably for real-time verification, of the particle range within the body part 112 of the patient 114 and the dose delivery into the body part 112 of the patient 114 under clinical conditions, thus, allowing a reduction of uncertainties in treatment planning.

Consequently, each detector element 132 as comprised by the verification unit 130 is designated for determining the prompt-gamma radiation 140 being generated by the interaction of the particles 118 with the irradiated body part 112 of the patient 114. For this purpose, the detector element 132 is designed for generating a measurable signal from the incident prompt-gamma radiation 140, wherein the measurable signal may, preferably, be selected from an electrical signal, specifically an electrical voltage or an electrical current. In particular, the detector element 132 may, thus, be selected from at least one of: a photomultiplier tube (PMT), a solid-state single-photon-sensitive device (silicon photomultiplier; SiPM), a charge-coupled device (CCD), a complementary metal-oxide-semiconductor (CMOS), or a quanta image sensor (QIS) chip.

However, other kinds of detector elements may also be feasible. If the verification unit 130 may, as illustrated in FIGS. 1 to 4B, comprise at least two individual detector elements 132, it is particularly preferred that the individual detector elements 132 are of the same type and kind in order to increase a comparability of the measured signals between the individual detector elements 132.

As further illustrated in FIG. 1, the verification unit 130 may, preferably, comprise a collimator unit 142 which is designated for collimating and shaping the prompt-gamma radiation 140 after having been generated by the interaction of the particles 118 with the body part 112 of the patient 112 but prior to entering the corresponding detector element 132. Using the illustrated collimator units 142 for collimating the prompt-gamma radiation 140 prior to a detection in the corresponding detector 132 element may, advantageously, result in a desired increase of a spatial resolution of the detection of the prompt-gamma radiation 140 within the body part 112 of the patient 114. However, it is also conceivable that the verification unit 140 may be provided without the collimator units 142.

In addition, the verification unit 140 may, further, comprise an evaluation device 144 which is designated for determining the information about the prompt-gamma radiation 140 as acquired by the detector element 132, in particular by evaluating the measurable signals as provided by the detector elements 132 to the evaluation device 144. For an exchange of the information, a wire-based connection 145 as schematically depicted in FIG. 1, or, alternatively or in addition, a wireless connection (not depicted here), between the detector elements 132 and the evaluation device 144 may be provided. The evaluation device 144 may, particularly, be designed for verifying the particle range and the dose delivery of the particles 118 as provided by the beam 116 to the body part 112 of the patient 114. For this purpose, the evaluation device 144 may comprise a fast analog-to-digital converter, preferably having a sampling rate of 10 ns, more preferably of 4 ns, more preferably of 1 ns or below. Herein, the fast analog-to-digital converter may, preferably, be selected from at least one of: a flash analog-to-digital converter (FADC), a field-programmable gate array (FPGA), a versa module eurocard (VME) digitizer, a time readout board (TRB), or an oscilloscope. However, other types of fast analog-to-digital converter may also be conceivable.

Further, the evaluation device 144 may be connected to a monitor 146 and a keyboard 148 which may, preferably, be located outside the device 110. Alternatively or in addition, a processing device (not depicted here) may also be connected, in a wire-bound or a wireless fashion, to the evaluation device 144, wherein the processing device may be designed for controlling the evaluation device 144, such as in a master-slave relationship. However, further kinds of processing devices may also be feasible.

In accordance with the present invention, a symmetry axis 149 of the verification unit 130 is located in a perpendicular manner with respect to the direction 124 of the propagation of the beam 116, resulting in an arrangement of the verification unit 130 in which the verification unit 130 is located in a manner that it determines the desired information about the prompt-gamma radiation 140 in an orientation which is perpendicular to the direction 124 of the propagation of the beam 116. Thus, the information about the prompt-gamma radiation 140 which is determined by the verification unit 130 comprises only components which are perpendicular to the direction 124 of the propagation of the beam 116. For this purpose, the verification unit 130 is designated for moving perpendicular to the direction 124 of the propagation of the beam 116, thus, allowing the verification unit 130 determining information about the prompt-gamma radiation 140 at at least two individual interaction points 150 of the particles 118 impinging the body part 112 of the patient 114. For further details, reference may be made to the description of FIGS. 4A and 4B below.

As illustrated in FIG. 1, the perpendicular arrangement of the symmetry axis 149 of the verification unit 130 with respect to the direction 124 of the propagation of the beam 116 is provided by a relative arrangement of a rotational gantry 152 and a patient positioning platform 154 which may both further comprised by the device 110. As schematically depicted in FIG. 1, the patient positioning platform 154 comprises a reception which is designated for receiving the patient 114, for moving the patient 114 into an appropriate position designated for receiving the treatment, and for maintaining the patient 114 in this position during the duration of the treatment. For this purpose, robotic instrumentation may, preferably, be employed for accurately positioning the patient 114 with regard to six directions of movement or rotation.

Further, the rotational gantry 152 is adapted to receive the patient positioning platform 154 and to rotate in a continuous manner or in arbitrary or predefined steps, preferably over a full circle of 360°, with respect to the patient positioning platform 154, whereby the beam 116 is delivered to the body part 112 of the patient 114 at any desired angle, specifically at an angle which may be specified by a treatment plan. In accordance with this embodiment, the rotational gantry 152 and/or the patient positioning platform 154 can be moved for adjusting the direction 124 of the propagation of the beam 116 with respect to the patient 114 in a desired manner. Thereby, a distance and/or a relative orientation between the rotational gantry 152 and the patient positioning platform 154 can be amended by moving a single part of the device 110.

According to this preferred embodiment of the device 110, the rotational gantry 152 may comprise a moveable side wall 156 and a moveable front wall 158, wherein the front wall 158 may be placed in a perpendicular fashion with respect to the side wall 156. As schematically depicted in FIG. 1, the beam delivering unit 120 may be coupled to the side wall 156 and be movable with the side wall 156 to different positions with respect to the patient positioning platform 154, whereas the verification unit 130 may be coupled to the front wall 158 and be movable with the front wall 158 to different positions with respect to the patient positioning platform 154 in a synchronized manner with the beam delivering unit 120. Since the front wall 158 may, preferably, assume a perpendicular orientation with respect to the side wall 156, the perpendicular arrangement of the symmetry axis 149 of the verification unit 130 with respect to the direction 124 of the propagation of the beam 116 can be maintained during the treatment of the patient 114 in a particularly easy fashion.

In a further embodiment of the present invention (not depicted here), both the beam delivering unit 120 and the verification unit 130 may be coupled to the side wall 156 and movable with the side wall 156 to different positions with respect to the patient positioning platform 154 in a synchronized manner, thereby maintaining the perpendicular arrangement of the symmetry axis 149 of the verification unit 130 with respect to the direction 124 of the propagation of the beam 116 during the treatment although only the side wall 156 may be moved while other parts of the device, such as the front wall 158 or the patient positioning platform 154, may be maintained in position.

In a further embodiment of the present invention (not depicted here), the beam delivering unit 120 may be provided in a vertical orientation or a nearly vertical orientation with respect to a plane being defined by the patient positioning platform 154, wherein the nearly vertical orientation refers to a deviation of ±15°, preferably of ±5°, from the vertical orientation, while the verification unit 130 may be provided in a perpendicular orientation thereto in order to avoid interference with movements of the patient positioning platform 154, preferably at an angle of 45°. As an alternative, the verification unit 130 may be movable around the patient positioning platform 154 to a desired position in order to avoid a conflict with the patient positioning platform 154.

Figure 2:
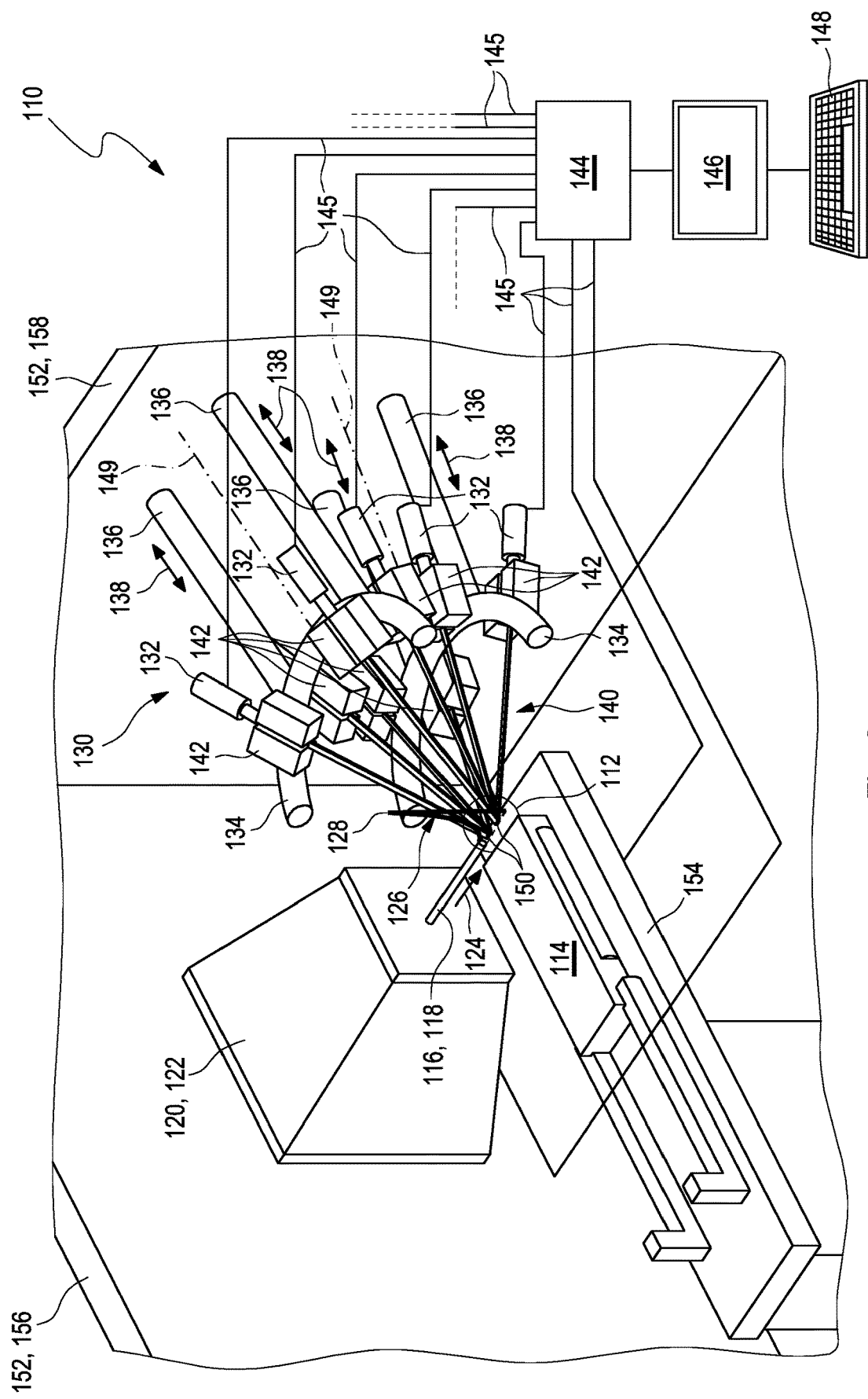
FIG. 2 illustrates a further preferred embodiment of the device for the monitoring of the treatment of the body part of the patient with the particle beam in a perspective view, wherein the device comprises a beam delivery unit in a side arrangement and a verification unit having eight individual detector elements.

FIG. 2 illustrates a further preferred embodiment of the device 110 according to the present invention in which the verification unit comprises eight individual detector elements 132. Herein, the symmetry axis 149 of the verification unit 150 is orthogonal to the direction 124 of the propagation of the beam 116, however, the detector elements 132 may rotate up to approximately ±140°. As schematically depicted, four of the detector elements 132 are applied to an individual support 134 in a manner that they can be jointly moved towards or away from the body part 112 of the patient 114. However, a further number of individual detector elements 132 or a different arrangement of the individual detector elements 132 may also be feasible. Thus, the treatment of the body part 112 of the patient 114 with the particle 118 as provided by the beam 116 may, preferably, be monitored at two or more different interaction points, whereby an accuracy of the verification of the particle range within the Bragg peak 138 compared to known devices according to the state of the art can be increased.

For a detailed description of further features as illustrated in FIG. 2, reference may be made to the description of FIG. 1 above.

FIG. 3 illustrates a further preferred embodiment of the device 110 according to the present invention in which the beam delivering unit 120 may be provided in a horizontal orientation or a nearly horizontal orientation with respect to the plane being defined by the patient positioning platform 154. As schematically depicted in FIG. 3, the beam delivering unit 120 which is provided here again in the form of the adjustable delivery nozzle 122 is designed for delivering the beam 116 in a perpendicular orientation with respect to the patient positioning platform 154. However, the beam delivering unit 120 may, alternatively, be designed for delivering the beam at an angle of 45±45°. Consequently, the verification unit 130 can always maintain the perpendicular orientation with respect to the direction 124 of the propagation of the beam 116 irrespective of a movement of the beam delivery unit 120.

For a detailed description of further features as illustrated in FIG. 3, reference may be made to the description of FIG. 1 above.

FIGS. 4A and 4B further illustrate the preferred embodiment according to FIG. 3 in a side view in which the detector elements 132 are moved between FIGS. 4A and 4B by using the individual members 136 of the support 134 away from the body part 112 of the patient 114. In this fashion, a distance 160 between two individual interaction points 150 can be adjusted, thereby setting a spatial resolution for the detection of prompt-gamma radiation 140. As result of using the at least two individual interaction points 150 for determining the information about the prompt-gamma radiation 140, the device 110 is designed for determining absolute values for the particle range within the body part 112 of the patient 114. As a result of determining the absolute values for the particle range, distances within the body part 112 of the patient 114 can be determined with a high spatial resolution, thereby, allowing a confinement of the treatment of the body part 112 by the particles 118 of the incident beam 116 to the desired particle range, in particular to the tumorous tissue comprising the tumorous modification introduced by cancer.

In a further embodiment of the present invention, the verification unit 130 may only comprise a single detector element 132, wherein, however, in order to be able to, nevertheless, determine the information about the prompt-gamma radiation 140 at the at least two individual interaction points 150, the single detector element 132 may, preferably, be designed for being placed at at least two different positions within the verification unit 130 with respect to the body part 112 of the patient 114. During a movement between a placement at the least two different positions the distance between the single detector element 132 and the body part 112 may be maintained for each position. In this embodiment, the single detector element 132 may, thus, being moved between the at least two different positions at a first time scale which is faster compared to a second time scale of moving the single detector element 132 towards or away from the body part 112 perpendicular to the direction 124 of the propagation of the beam 116, whereby the distance between the individual interaction points can be adjusted as described above. Consequently, FIGS. 1, 3, 4A and 4B can be considered as illustrating this embodiment when showing the single detector element 132 at the two different positions at the same time.

Whereas using the single detector element 132 may, in particular due to its simplicity be advantageous for the purpose of quality assurance of the device, at least two, preferably four, six, eight or twelve detector elements 132 may, however, be preferred for an actual treatment of the patient 114 since the at least two individual detector elements 132 may allow increasing a sensitivity and, therefore, a spatial resolution of the determination of the particle range within the body part 112 of the patient 114.

LIST OF REFERENCE NUMBERS 110 device
112 body
114 patient
116 beam
118 particles
120 beam delivering unit
122 adjustable delivery nozzle
124 direction of propagation
126 Bragg curve
128 Bragg peak
130 verification unit
132 detector element
134 support
136 individual member
138 arrow
140 prompt-gamma radiation
142 collimator unit
144 evaluation device
145 wire-based connection
146 monitor
148 keyboard
149 symmetry axis
150 interaction point
152 rotational gantry
154 patient positioning platform
156 side wall
158 front wall
160 distance

The invention claimed is:

1. A device for monitoring a treatment of a body part of a patient with a beam comprising particles, the device comprising:
   a beam delivering unit designated for delivering a beam comprising particles and adjusting a direction of propagation of the beam onto a body part of a patient;
   a verification unit designated for verifying a range and a dose delivery of the particles provided by the beam to the body part of the patient by determining information about prompt-gamma radiation generated by an interaction of the particles with the body part of the patient at at least two individual interaction points, wherein the verification unit comprises a symmetry axis which is symmetrical with respect to the at least two individual interaction points and which is located perpendicular with respect to the direction of the propagation of the beam, wherein the symmetry axis relates to a set-up and an arrangement of the verification unit in which two halves of the verification unit being generated by the symmetry axis are identical with respect to each other; and
   a single rotational gantry and a patient positioning platform, wherein the patient positioning platform is designated for receiving the patient, wherein at least one of the gantry and the patient positioning platform is movable with respect to the other, wherein the gantry comprises a moveable side wall and a moveable front wall, wherein the front wall is placed perpendicular with respect to the side wall, wherein the direction of the propagation of the beam is adjustable to different positions with respect to the body part of the patient.

2. The device of claim 1, wherein both the beam delivering unit and the verification unit are coupled to and movable with the side wall to different positions with respect to the patient positioning platform in a synchronized manner.

3. The device of claim 1, wherein the beam delivering unit is coupled to and movable with the side wall to different positions with respect to the patient positioning platform, and wherein the verification unit is coupled to and movable with the front wall to different positions with respect to the patient positioning platform in a synchronized manner with the beam delivering unit.

4. The device of claim 1, wherein the beam delivering unit is provided in a fixed position with respect to the patient positioning platform, wherein the beam delivering unit is designated for delivering the beam in any orientation with respect to the patient positioning platform, and wherein the verification unit is movable to different positions with respect to a plane determined by the patient positioning platform.

5. The device of claim 1, wherein the verification unit comprises at least one detector element, wherein the detector element is designated for determining the prompt-gamma radiation generated by the interaction of the particles with the body part of the patient.

6. The device of claim 5, wherein the verification unit comprises at least two individual detector elements, wherein the at least two detector elements are spaced apart with respect to each other in a symmetrical manner with respect to the symmetry axis of the verification unit, wherein each detector element is designated for being movable towards or away from the body part of the patient perpendicular to the direction of the propagation of the beam in a manner that a distance between each detector element and the body part of the patient is equal for each detector element.

7. The device of claim 5, wherein the verification unit comprises a single detector element, wherein the detector element is designated for being placed at at least two different positions within the verification unit with respect to the body part of the patient in a manner that a distance between the detector element and the body part of the patient is maintained for each different position.

8. The device of claim 5, wherein the verification unit further comprises a collimator unit for collimating and shaping the prompt-gamma radiation generated by the interaction of the particles with the body part of the patient prior to entering the at least one detector element.

9. The device of claim 5, wherein the verification unit further comprises an evaluation device, wherein the evaluation device is designated for verifying the range and the dose delivery of the particles provided by the beam to the body part of the patient based on the information about the prompt-gamma radiation determined by the at least one detector element.

10. A method for monitoring a treatment of a body part of a patient with a beam comprising particles, the method comprising the steps of:
   providing the device of claim 1;
   delivering a beam comprising particles and adjusting a direction of propagation of the beam onto a body part of a patient;

determining information about prompt-gamma radiation generated by an interaction of the particles with the body part of the patient at at least two individual interaction points of the beam comprising the particles with the body part of the patient; and verifying a range and a dose delivery of the particles provided by the beam to the body part of the patient.

11. The method of claim 10, wherein the determining the information about the prompt-gamma radiation comprises specifying at least one position along the direction of the propagation of the beam by moving at least one detector element comprised by the verification unit perpendicular to the direction of the propagation of the beam;

moving an individual member of a support further comprised by the verification unit, wherein the at least one detector element is applied to the individual member, wherein the individual member is moved towards or away from the body part of the patient in a manner that the position along the direction of the propagation of the beam is focused or defocused, whereby a spatial resolution for the detection of the prompt-gamma radiation is set; and detecting the signal generated by the interaction of the prompt gamma radiation with the at least one detector element.

12. The method of claim 11, wherein the determining information about the prompt-gamma radiation further comprises determining a multitude of angular cross-sections between the particles and the body part of the patient, wherein each angular cross-section is determined for a different emission angle of 30° to 150°; and evaluating an energy of the beam and of the prompt-gamma radiation generated by the interaction of the particles with the body part of the patient for each interaction point.

13. The method of claim 12, wherein the evaluating of the energy of the beam and of the prompt-gamma radiation for each interaction point comprises reconstructing a detection line between the interaction point within the body part of the patient and the at least one detector element;

intersecting the detection line with the direction of the propagation of the beam, thereby detecting the interaction point; and determining a multitude of interaction points with respect to the energy and the angular cross-section, whereby the range and the dose delivery of the particles provided by the beam to the body part of the patient are verified.

14. The device of claim 1, having a computer program product comprising executable instructions for performing a method comprising:

delivering the beam comprising the particles and adjusting the direction of propagation of the beam onto the body part of the patient;

determining information about prompt-gamma radiation generated by the interaction of the particles with the body part of the patient at the at least two individual interaction points of the beam comprising the particles with the body part of the patient; and verifying the range and the dose delivery of the particles provided by the beam to the body part of the patient.

* * * * *